US00PP23033P2

(12) United States Plant Patent
Eggleton

(10) Patent No.: US PP23,033 P2
(45) Date of Patent: Sep. 11, 2012

(54) ***VIOLA* PLANT NAMED 'SMEV2'**

(50) Latin Name: *Viola×hybrida*
Varietal Denomination: SMEV2

(76) Inventor: Steve Eggleton, Wonga Park (AU)

( * ) Notice: Subject to any disclaimer, the term of this patent is extended or adjusted under 35 U.S.C. 154(b) by 203 days.

(21) Appl. No.: 12/804,662

(22) Filed: Jul. 27, 2010

Related U.S. Application Data

(60) Provisional application No. 61/273,275, filed on Aug. 3, 2009.

(51) Int. Cl.
*A01H 5/00* (2006.01)

(52) U.S. Cl. ..... Plt./323

(58) Field of Classification Search ..... Plt./323
See application file for complete search history.

*Primary Examiner* — Howard Locker

(57) ABSTRACT

A new cultivar of *Viola* named 'SMEV2' that is distinguishable by compact dome-shaped habit, green glossy foliage, and large soft yellow flowers. In combination these traits set 'SMEV2' apart from all other existing varieties of *Viola* known to the inventor.

2 Drawing Sheets

Genus: *VIOLA*.
Species: ×*hybrida*.
Denomination: 'SMEV2'.

BACKGROUND OF THE INVENTION

The present invention relates to a new and distinct cultivar of *VIOLA* known commonly as violet and grown for use in border, container, and landscape. The new invention from the family Violaceae is known botanically as *VIOLA×hybrida* and will be referred to hereinafter by the cultivar name 'SMEV2'.

'SMEV2' resulted from a formal breeding program developed by the inventor, and conducted in Wonga Park, Victoria, Australia with the goal of producing a series of perennial *Viola* exhibiting a range of flower color. The breeding program commenced in 2002.

'SMEV2' is a hybrid seedling selection that resulted from controlled cross-pollination of the female parent, *Viola* 'Lord Primrose' (U.S. Plant Pat. No. 18,253) and the male parent, *Viola* 'Painted Porcelain' (non-patented). Seed was collected and sown in early 2005 and raised to flowering. From an approximate 150 seedlings, five were selected by the inventor, and then propagated asexually, by cuttings. From these 'SMEV2' was selected in 2005 based on the criteria of habit, flower dimensions, flower color, and prolific flower number.

The closest comparison plants known to the inventor are the two parent varieties, 'Lord Primrose' and 'Painted Porcelain'. 'SMEV2' is distinguishable from both parents by flower color. Whereas the flowers of 'SMEV2' are solid yellow in color, the flowers of 'Lady Primrose' are predominantly violet in color and exhibit a mid-yellow blotch or eye; and the flowers of 'Painted Porcelain' are light violet in color and exhibit a dark violet blotch or eye.

The unique traits exhibited by 'SMEV2' are compact dome-shaped habit, glossy green foliage, and numerous large scented flowers that are soft yellow in color, and held on short peduncles. Blooming occurs spring through fall. After six months of growth from a rooted cutting the dimensions of 'SMEV2' are 20 cm. in height and 20 cm. in width. Cultural requirements include shade to filtered sunlight, moist organic soil, and regular water. 'SMEV2' is hardy in USDA Zone 5.

The first asexual reproduction of 'SMEV2' was accomplished in 2005 in a cultivated area of Victoria, Australia. Asexual propagation was accomplished by the inventor, using the method, of softwood cuttings. Since that time 'SMEV2' has been determined stable and true to type in subsequent generations of asexual propagation.

SUMMARY OF THE INVENTION

The following traits have been repeatedly observed and represent the distinguishing characteristics of the new *Viola* cultivar named 'SMEV2'. These traits in combination distinguish 'SMEV2' from all other existing varieties of *Viola* known to the inventor. 'SMEV2' has not been tested under all possible conditions and phenotypic differences may be observed with variations in environmental, climatic, and cultural conditions, however, without any variance in genotype.

1. 'SMEV2' exhibits compact dome-shaped habit.
2. 'SMEV2' exhibits green glossy foliage.
3. 'SMEV2' produces numerous large flowers on short peduncles.
4. The flowers of 'SMEV2' are soft yellow in color, slightly fading towards the outer petal margins.
5. The flowers of 'SMEV2' are pleasantly fragrant with the characteristic perfume of violets.
6. After one year of growth from a rooted cutting 'SMEV2' is 20 cm. in height including the flowers, and 20 cm. in width.
7. 'SMEV2' is hardy in USDA Zone 5.
8. 'SMEV2' blooms spring through fall.

BRIEF DESCRIPTION OF THE DRAWINGS

The accompanying color drawings illustrate the overall appearance of the new *Viola* cultivar named 'SMEV2' showing color as true as is reasonably possible to obtain in color reproductions of this type. Color in the drawings may differ from the color values cited in the detailed botanical description, which accurately describe the actual color of the new variety 'SMEV2'.

The drawing labeled

The drawing labeled

Figure 1:
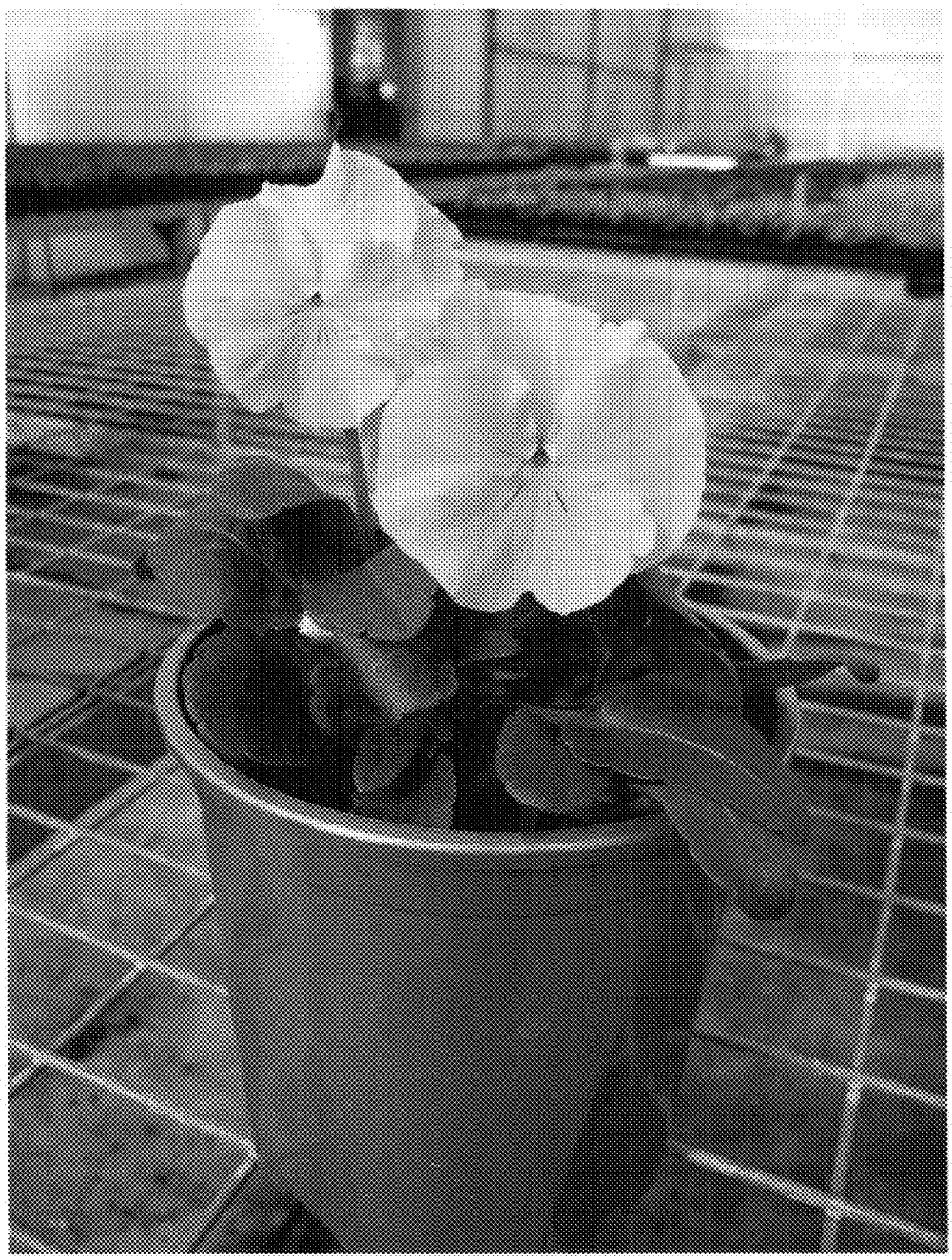
FIG. 1 depicts a 3 months plant in first bloom, grown in a 10 cm. container.
Figure 2:
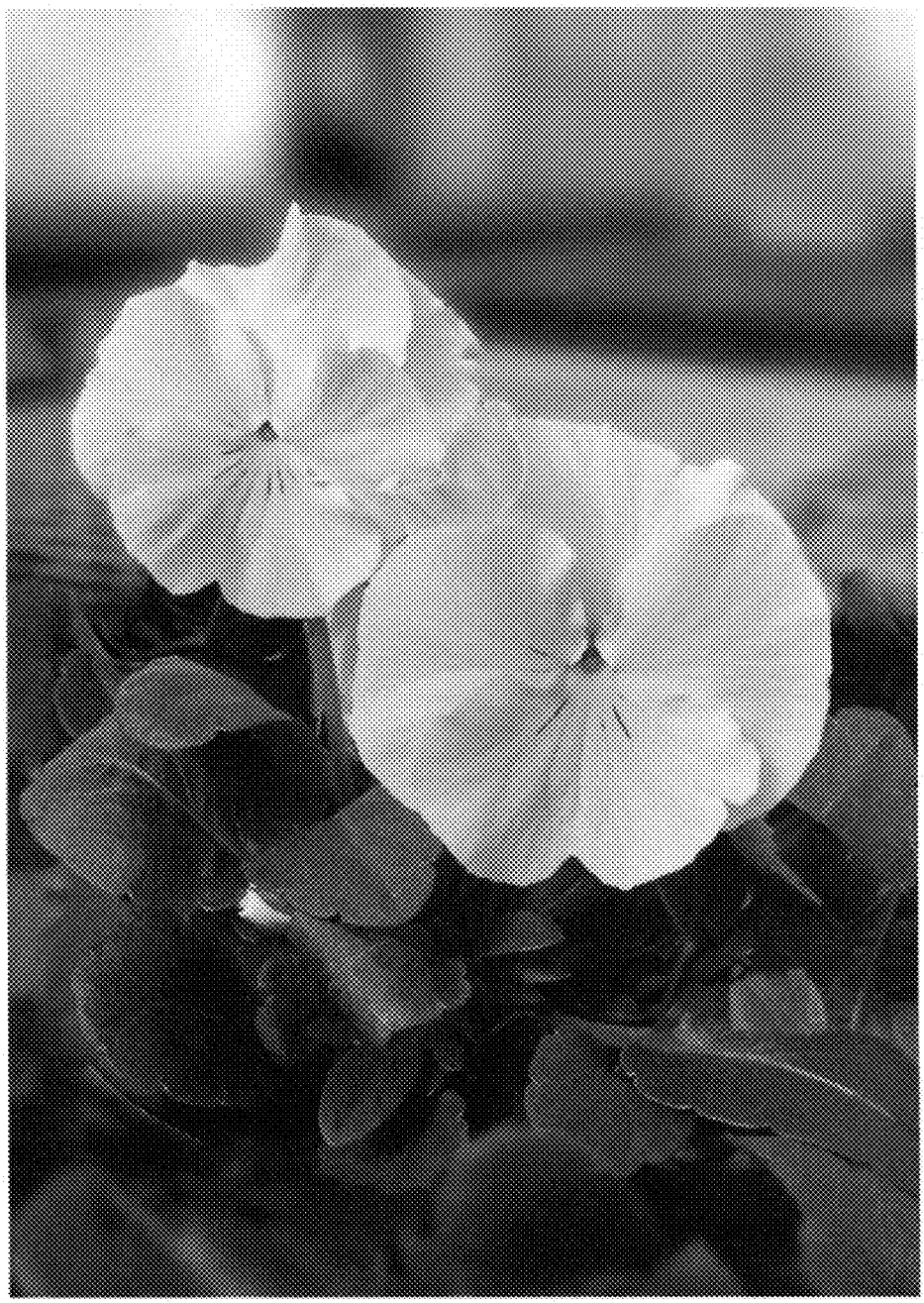
FIG. 2 depicts a close-up view of the flowers on the plant shown in FIG. 1.

Both drawings were made from a plant which has been grown in a well-ventilated unheated greenhouse in Victoria, Australia. No pinching or chemical growth regulators have been employed.

Both drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Viola* cultivar named 'SMEV2'. Observations and measurements were collected in Arroyo Grande, Calif. during the month of July from a two months old plant, grown from an unrooted cutting, and in its first flower. The observed plant was grown out of doors in a 6 cm liner pot. Color determinations were made in accordance with The 2001 Royal Horticultural Society Colour Chart from London, England, except where general color terms of ordinary dictionary significance are used.

Botanical classification: *VIOLA×hybrida* 'SMEV2'.
Family: Violaceae.
Genus: *VIOLA*.
Species: *×hybrida*.
Denomination: 'SMEV2'.
Common name: Violet.
Habit: Compact.
Shape: Dome-shaped.
Type: Perennial.
Commercial category: Ornamental.
Use: Border, container, and in the landscape.
Suggested commercial container size: 10 cm. pot and 1-liter container.
Parentage: *VIOLA×hybrida* 'SMEV2' is a hybrid seedling selection that resulted from the controlled cross-pollination of the following parents:
*Female parent.*—*Viola* 'Lord Primrose' (U.S. Plant Pat. No. 18,253).
*Male parent.*—*Viola* 'Painted Porcelain' (non-patented).
Propagation method: Softwood cuttings.
Rooting system: Fine and fibrous.
Vigor: Moderate.
Time to develop roots (range): 14-20 days to develop roots on an initial cutting.
Temperature to develop roots: The recommended air temperature is 20-21° Centigrade.
Crop time (range): Under summer growing conditions, 'SMEV2' will flower and be saleable in a 10 cm container in flower after 3 months of growing from an unrooted cutting. During winter and spring months in an unheated greenhouse 'SMEV2' flowers and is saleable in 4-6 months depending on light levels and day length.
Plant dimensions: 20 cm. in height including the flowers, and 20 cm. in width.
Cultural requirements: Grow in moist organic soil, shade to filtered sunlight with regular water.
Pest or disease resistance or susceptibility: No particular disease or pest resistance or susceptibility is known to the inventor.
Hardiness: USDA Zone 5.
Stem:
*Branching*.—Basal
*Stem color*.—N144C. .
*Stem length* (*average*).—5 cm.
*Stem width*.—0.25 cm.
*Stem shape*.—Cylindrical.
*Stem surface*.—Glabrous.
*Internode* (*average*).—0.75 cm.
Foliage:
*Type*.—Evergreen.
*Leaf arrangement*.—Alternate.
*Leaf division*.—Simple.
*Leaf quantity* (*average*).—6.
*Margin*.—Crenate.
*Leaf shape*.—Ovate.
*Leaf length* (*range*).—2 cm-3.50 cm.
*Leaf width* (*range*).—1.50 cm-2.25 cm.
*Leaf color* (*abaxial surface*).—137C.
*Leaf color* (*adaxial surface*).—137A.
*Leaf base*.—Rounded.
*Leaf apex*.—Rounded.
*Venation*.—Pinnate.
*Vein color* (*abaxial and adaxial surfaces*).—137C.
*Leaf surface* (*abaxial and adaxial*).—Glabrous.
*Leaf attachment*.—Petiolate.
*Petiole color*.—138B.
*Petiole dimensions* (*average*).—2 cm. in length and 1 mm. in width.
*Petiole shape*.—Sulcate.
*Petiole surface*.—Glabrous.
*Stipules*.—Present and persistent.
*Stipule form*.—Leaf-like.
*Stipule margin*.—Cleft.
*Stipule apex*.—Rounded.
*Stipule base*.—Truncate.
*Stipule color*.—138B.
*Stipule surface* (*abaxial and adaxial*).—Glabrous.
*Stipule attachment*.—Sessile.
*Stipule dimensions* (*average*).—1.50 cm. in length and 0.50 cm. in width.
*Fragrance*.—None observed.
Inflorescence:
*Inflorescence*.—Solitary flower.
*Inflorescence quantity* (*average*).—3.
*Aspect* (*range*).—Facing outward to pendant.
*Inflorescence width*.—2.75 cm.
*Inflorescence length*.—3.25 cm.
*Inflorescence depth*.—2 cm.
*Inflorescence arrangement*.—Terminal inflorescence.
*Inflorescence color on abaxial surface*.—4A, fading to 4C.
*Inflorescence color on adaxial surface*.—4A, fading to 4C.
*Inflorescence shape*.—Rotate.
*Blooming seasons*.—Spring through fall.
*Peduncle length* (*range*).—5.50 cm-7 cm.
*Peduncle width*.—3 mm.
*Peduncle shape*.—Sub-cylindrical.
*Peduncle surface*.—Glabrous.
*Peduncle color*.—144B.
*Peduncle strength*.—Flexible.
*Bud color*.—143B.
*Bud shape*.—Elongated oval.
*Bud dimensions* (*average*).—1.30 cm. in length and 0.40 cm, in width.
*Bud surface*.—Glabrous.
*Bud apex*.—Rounded.

*Corolla tube depth.*—6 mm.
*Petal quantity.*—5 in number.
*Spur.*—1 present on anterior petal.
*Spur color.*—144B.
*Spur dimensions.*—3 mm. in length and 1.50 mm. in width.
*Petal shape* (*range*).—Reniform to obcordate.
*Petals fused or unfused.*—Unfused.
*Petal apex* (*range*).—Obtuse to obcordate.
*Petal base.*—Truncate to cuneate.
*Petal margin* (*range*).—Entire to lightly crisped.
*Petal length* (*range*).—1.25 cm-1.75 cm.
*Petal width* (*range*).—1.75 cm-cm.
*Petal color on abaxial surface.*—4A, fading to 4C.
*Petal color on adaxial surface.*—4A, fading to 4C.
*Petal surface* (*abaxial and adaxial*).—Glabrous.
*Petal appearance.*—Iridescent.
*Petal veins.*—Veins appear as slight depressions of same color as surrounding tissue and are barely evident, except for short "lines" of dark purple veining within lower petals, length 5 mm-8 mm, width 0.5 mm, color N92A, radiating and commencing approximately 5 mm from petal base.
*Calyx shape.*—Stellate.
*Calyx diameter.*—2 cm.
*Sepals.*—5 in number.
*Sepal dimensions.*—1 cm. in length and 0.40 cm. in width.
*Fused or unfused.*—Sepals unfused.
*Sepal color* (*abaxial and adaxial surfaces*).—138A.
*Sepal apex.*—Acute.
*Sepal base.*—Truncate.
*Sepal surface* (*abaxial and adaxial*).—Glabrous.
*Sepal margin.*—Entire.
*Sepal shape.*—Lanceolate.
*Inflorescence self-cleaning or persistent.*—Self-cleaning.
*Inflorescence fragrance.*—Mild scent.
*Lastingness of inflorescence* (*range*).—5-7 days.

Reproductive organs:
*Stamen quantity.*—5 joined around ovary.
*Stamen length.*—4 mm.
*Stamen color.*—145D.
*Anther length.*—<1 mm. appendage to stamen.
*Anther width.*—2.50 mm.
*Anther color.*—164A.
*Pollen color.*—155C.
*Pollen quantity* (*range*).—Moderate to heavy.
*Pistil quantity.*—1.
*Pistil height.*—6.5 mm.
*Style height.*—1 mm.
*Style color.*—N144A.
*Stigma dimensions.*—<1 mm. in height and 1 mm. in diameter.
*Stigma color.*—N144A.
*Stigma shape.*—Globular.
*Stigma surface.*—Glandular.
*Ovary position.*—Superior.
*Ovary color.*—N144A.
*Ovary shape.*—Dome-shaped.
*Ovary dimensions.*—6 mm. in height and 3 mm. in width.

Seed: None observed to date.

The invention claimed is:

1. A new and distinct cultivar of *Viola* plant named 'SMEV2' as described and illustrated herein.

* * * * *